United States Patent [19]
Lindstrom et al.

[11] Patent Number: 5,774,519
[45] Date of Patent: Jun. 30, 1998

[54] METHOD OF AND APPARATUS FOR CALIBRATION OF CT SCANNERS

[75] Inventors: Walter W. Lindstrom, Rockport; John Scott McCauley, Jr., Brookline, both of Mass.

[73] Assignee: Analogic Corporation, Peabody, Mass.

[21] Appl. No.: 791,384

[22] Filed: Jan. 30, 1997

[51] Int. Cl.[6] ..................................................... A61B 6/03
[52] U.S. Cl. .............................................. 378/18; 378/901
[58] Field of Search ................................... 378/4, 18, 901

[56] References Cited

U.S. PATENT DOCUMENTS

| | | | |
|---|---|---|---|
| 4,352,020 | 9/1982 | Horiba et al. | 378/18 |
| 5,214,578 | 5/1993 | Cornuejols et al. | 378/207 |
| 5,442,674 | 8/1995 | Picard et al. | 378/20 |

*Primary Examiner*—David P. Porta
*Assistant Examiner*—David Vernon Bruce
*Attorney, Agent, or Firm*—Lappin & Kusmer LLP

[57] ABSTRACT

In an improved CT scanner calibration method and apparatus, a radiation beam, for example an x-ray beam, is directed at a plurality of radiation detectors. The beam is attenuated by a phantom of known attenuation characteristics. The detectors generate measured attenuation data from the attenuated beam. The measured attenuation data is back-projected to generate a measured phantom image. The measured phantom image is converted to an ideal phantom image. The ideal phantom image is forward projected to generate ideal attenuation data. Calibration values for each detector channel in the scanner are generated by cross-referencing the ideal and measured attenuation data. In a preferred embodiment, this cross-referenced data is compressed and stored in a look-up table for referencing during later interrogation of subjects. This technique takes advantage of the inherent mechanical accuracy of the scanner to perform calibration, rather than imposing requirements of phantom geometry precision or exact phantom placement

18 Claims, 11 Drawing Sheets

METHOD OF AND APPARATUS FOR CALIBRATION OF CT SCANNERS

FIELD OF THE INVENTION

The present invention relates generally to computed tomography (CT) scanners, and more particularly to a method and apparatus for calibrating such scanners.

BACKGROUND THE INVENTION

In a CT scanner of the third generation type, a beam of energy, usually in the form of a broad band X-ray beam, emanates from a focal spot of a beam source through a subject and is directed toward a sensor array. The sensor array comprises a plurality of X-ray detectors in a curved linear array having a center of curvature at the focal spot. The X-ray beam is thus generally fan-shaped. The X-ray source and sensor array are fixed relative to each other and rotate about an object or human subject during a scan. This provides a series of projections of the subject over a range of orientations. At each orientation or view, the beam is attenuated by the subject. Sensor data at each orientation is collected and processed through detection channels (one for each detector) to provide a cross-sectional image of the patient.

Uniformity between individual detection channels is essential. Otherwise, anomalies may occur in the collected data. A consequence of data anomalies are image distortions, commonly referred to as artifacts. There are many reasons for nonuniformity in the detector channels, for example lack of uniformity of solid state detectors due to radiation damage, energy dependence of the photodiodes used as part of the solid state detectors, differences in the transfer functions for each of the detector channels, etc. For this reason, periodic calibration of the detector array is required.

A common method for calibration employs a device known as a phantom. Phantoms provide known attenuation paths for beams passing therethrough. Any non-uniformity exhibited during calibration using phantoms provides an error value which is fed back to correct and calibrate the channels so that they are uniform for subsequent use when imaging a patient.

The attenuation is usually exponential. This means that, for a beam of input intensity $I_0$, the intensity I of the beam escaping a length L of material with a linear attenuation coefficient of $\mu$ is given by the relation:

$$I = I_0 e^{-\mu L}$$

so that x-ray energy absorption is a function of the both the density of the material and path length through which the x-ray beams pass.

Various techniques employing phantoms to calibrate the detector channels have been used. Some of these techniques use plastic cylinders filled with water and solid plastic cylinders of various predetermined densities. However, the linear attenuation coefficient $\mu$ is a function of the x-ray energy E and any water phantom typically has a plastic container to hold the water, so $\mu$ is a function of both the x-ray energy, which changes continuously along the path through the phantom, and the position, whether in plastic or water or air. Also, plastic usually has imperfections of different density at different points. It therefore follows that a more complete relation, taking these factors into account is:

$$I = I_0 e^{-\int \mu(E,s) ds}$$

where the integral is over the path s, with $\mu(E,s)$ changing along the path.

The beam of energy generated by the X-ray source is usually broadband exhibiting a wide energy spectrum having a variety of photon energies. As an x-ray beam traverses an object of a predetermined density, greater absorption of low energy photons tends to occur initially, with high energy photons in the x-ray energy range being absorbed further along the path through the object, a phenomenon referred to as "beam hardening". This means, for example, that uncorrected images will show the center of a water phantom or through soft tissue on a human subject (soft tissue having a density similar to water) to appear to have a lower $\mu$ value, because, on average, the x-ray photons probing this region will have propagated along a longer path, through more water, or tissue, than those photons probing outer regions. The net result is that the absorption is not constant across the spectral band of the beam. Water makes for a good absorption reference, and is generally used as a reference beam in CT images. Typically, the intensity value of water in a CT image is set at 0 Hounsfield Units (HU), and is therefore advantageous to use as a phantom. In medical imaging, water is the preferred phantom material because it is inexpensive in a pure form, for example distilled water. In addition it is very uniformly dense in liquid form in normal clinical settings. Another important reason for using water is that it is the main component of tissues in the human body.

Historically, the first attempt to correct for the wide range of x-ray energies available from conventional x-ray tubes was made by Hounsfield who employed a hardware solution, namely placing the patient's head within a water box. Later, for whole body scanning where a water box was impractical, Hounsfield surrounded the patient with bolus bags to partially accomplish the same effect. Since this unit had a fixed-anode x-ray tube, off-focal effects were negligible and the water box made the scatter effects very small.

The next step was to replace the water bag with a phenomenological $\mu L$-based correction, using a circular water phantom for this purpose. Since this was a second-generation CT scanner with a fixed-anode x-ray tube, scatter and off-focal effects could be made negligible through hardware design. Each detector was calibrated individually, without assuming that the data collection system was linear, which it was not.

More recently, flat sheets of polyethylene of various stepwise thicknesses are employed for phantoms. The discrete $\mu L$ points collected on the phantoms are fit at values of approximately 1, 2, 3, 4, 5, 6 to a fourth order polynomial. This technique has the advantage of limited amounts of scattered radiation and uniform contribution to detector response as the response varies with the attenuation. However, flat phantoms do not simulate the scattered radiation produced by a real patient, and until robust scatter correction becomes available, it will be difficult to achieve good results with either circular test phantoms or patients.

Others are known to use precisely-centered phantoms comprising plastic and/or water sealed in plastic. Utilizing precise size control through precision machining and precise composition through materials of known density, coupled with precise positioning of the phantom within the scan field, attenuation paths of known $\mu L$ can be compiled. In this way, actual measurements of attenuation along these known paths can be compared with calculated ideal attenuations and a calibration can be made. In addition, because each individual detector in a third-generation CT samples exactly the same chord length for a centered cylindrical object as the source and detector rotate about the phantom, excellent photon statistics are obtained for a selected sparse set of measurements on each detector. The difficulty with this is that, with the exception of detectors which may be symmetrical to one another relative to the center ray, no two detectors measure the same attenuation, and it is difficult to interpolate between the few (4–6) measured $\mu$L data points. In addition considerable time and effort must be spent in aligning the phantoms in the scan field.

A problem with this approach is the difficulty of interpolating the $\mu$L nonlinearity correction from the selected sparse set of measurements. Even though the correction needed for the selected points is known to excellent precision, interpolation between them requires superb spectral uniformity of the detector modules used, as well as superb linearity of the entire data collection chain including any analog circuitry and the data acquisition system (DAS). In particular, range switching glitches must be strictly avoided and analog filters must be matched to 100 PPM.

U.S. Pat. No. 4,352,020 discloses a method and apparatus for calibration of CT scanner detector channels wherein calibration data is collected by imaging a plurality of phantom elements. The phantom elements are formed in precise circular geometry and the center of each phantom is placed precisely at the center of rotation, or isocenter, of the scanner and detectors. Data collected during measurement of the phantom is stored in a calibration look-up table. When a subject is later interrogated by the scanner, collected data is modulated by the calibration look-up table. In this manner, the image of the subject is corrected by the calibration data for correcting for any errors in the detector array. This method is generally complicated and time consuming due to the alignment of the phantoms and costly due to the precise machining. In addition, it is nearly impossible to obtain uniformity in plastic materials, and generally plastic phantoms are used in this procedure. Furthermore, after the calibration values for the system are configured for the plastic phantom, they must be re-converted to Housfield units—and redefined for tissue-like water.

U.S. Pat. No. 5,214,578 discloses a method and apparatus for detector calibration employing a single, circular phantom. The single phantom is disposed in the radiation beam path at a position which is a distance from the axis of rotation of the scanner. This provides a range of path lengths through the phantom for each detector channel. The path length through the phantom depends on the angular position of the scanner relative to the phantom during the scan. An advantage of this is that a single phantom handling and alignment operation is required instead of multiple phantoms and operations. However, this technique requires a homogeneous calibration phantom of a precise geometry, for example a perfect cylinder. Furthermore, the detector uniformity must be sufficient to precisely determine the center of this perfect phantom. Additionally, the interpolation curve or chart must fit to an assumed functional form, for example a polynomial. This limitation of conforming the data to a polynomial causes the system to be calibrated over a narrow range of attenuation values. For this reason, different calibration tables are required for different size bodies, and different parts on the bodies—adding to system complexity and cost, and complicating calibration procedures.

SUMMARY AND OBJECTS OF THE INVENTION

The present invention overcomes the limitations cited above by performing detector calibration taking advantage of the inherent mechanical accuracy of the scanner rather by imposing additional requirements of phantom geometry precision or exact phantom placement.

Because no assumptions are made as to the precise geometrical shape or wall perfection of the phantom, the present invention is compatible with inexpensive, imprecisely positioned and irregular shaped calibration phantoms, driving phantom and operational costs down. In addition, the present invention eliminates the need for separate calibrations for different parts of the body, saving time and money. With fewer constraints on the geometry of the phantom, water phantoms more closely representative of patient anatomy may be employed, rather than cylinders. In addition, artifacts incurred during calibration due to scattering can be lessened by using phantom shapes of irregular geometry.

Further, in accordance with another aspect of the present invention, by including the scan of the "empty scan aperture" (the opening between the source and detectors) as well as scans of the selective water phantoms, the present invention is operable with less than perfect X-ray windows (the portion of the covering or skin of the scanner positioned between the X-ray source and detectors within the scan aperture) lowering the cost of the overall system. In addition, flatness-of-field is excellent throughout the entire acquisition field.

Because no assumptions are made on the functional form of the correction, the present invention will operate with data acquisition systems of imperfect linearity. In addition, the functional form of the correction is not limited to a predictable assumed polynomial form, as in prior art methods. By alleviating this limitation, the calibrated system is operable over a larger range of attenuation $\mu$L values.

In accordance with another aspect of the present invention, the calibration data is interpolated between known points using a "seed curve" determined from known detector characteristics. This allows for compensation of non-linear behavior in the system anywhere in the data acquisition chain.

With the above advantages in mind, the present invention is directed to an apparatus for and method of calibrating radiation detectors in a CT scanner. The method of the invention comprises the step of first directing a radiation beam at a plurality of radiation detectors. The beam is directed through a phantom having known attenuation characteristics. The phantom attenuates the beam and the detectors generate measured attenuation data from the attenuated beam. Next, the measured attenuation data is back-projected to generate a measured phantom image. In a preferred embodiment, a seed curve of approximate detector calibration characteristics is used here to flatten the measured image. Following this, the measured phantom image is converted to an ideal phantom image using the known phantom attenuation characteristics. This ideal phantom image is forward projected to generate ideal attenuation data. Calibration values are generated for each detector by cross-referencing the ideal and measured attenuation data.

In a preferred embodiment, a seed curve of known approximate detector characteristics is used to interpolate between and extrapolate from calibration values generated by the calibration method. When a subject, for example a patient is scanned, the measured subject data is applied to the calibration values to generate calibrated subject data. This calibrated subject data is back projected to generate a calibrated subject image.

In a preferred embodiment, the radiation beam comprises an X-ray beam. The phantom is preferably a water phantom of imprecise geometry and placed at an imprecise location in the beam path, alleviating cost in phantom formation and handling costs Further, while the preferred embodiment is described as a third generation CT scanner, the various aspects of the present invention can be applied to other types of scanners such as fourth generation machines.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
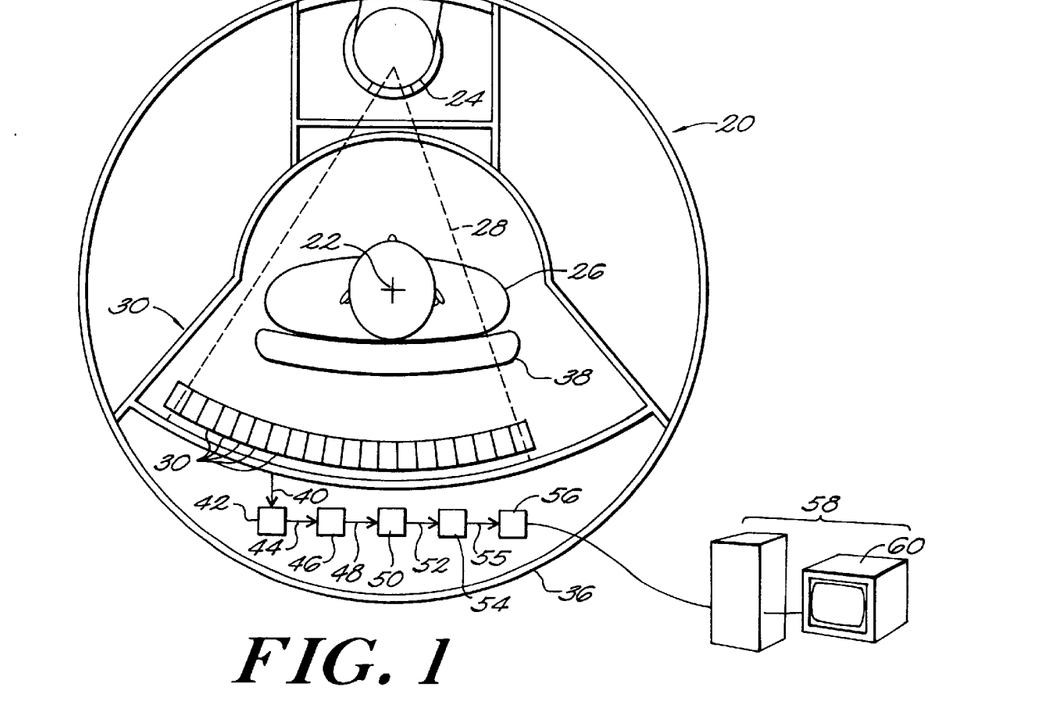
FIG. 1 is an axial view of a CT scanner system in accordance with the present invention.

FIG. 1 illustrates an exemplary third generation CT scanner 20, incorporating the principles of the present invention. The scanner 20 includes a radiation source 24 and a detector assembly 30 comprising an array of detectors 32. The source 24 and detector assembly 30 rotate about a rotation axis 22 extending normal to the FIG. 1 view. The subject 26 to be scanned, for example a patient, is positioned along the axis 22.

The radiation source 24 emits a beam of radiation 28, for example an X-ray beam, along a scanning plane substantially normal to the rotation axis 22. The beam 28 penetrates through the subject 26, and is incident on detectors 32. During penetration of the subject, the beam 28 undergoes a varying degree of absorption or attenuation. The detectors 32 are sensitive to the incident beam and generate detector signals 40 proportional to the amount of transmission through the subject.

In a preferred embodiment, the detector array 30 comprises 384 detectors 32 in a linear array. The array covers an arc of approximately 48°. The number of detector elements and the extent of the arc angle may vary. The source 24 and detector assembly 30 are mounted on a disk 36. The disk 36 allows for smooth and rapid rotation of the source 20 and detector assembly 30 about the subject. The subject 26 may be supported by a table 38 which is preferably transparent to the beam 28.

Detector signals 40 generated by the detector array 30 are applied to a data acquisition system (DAS), which generates therefrom a set of raw data signals 44. The raw data signals 44 are collected in the DAS 42 as the disk 36 rotates and different views of the subject are taken at a plurality of beam angles. The collection of raw data signals 44 is transmitted to a correction filter 46 which performs various linear corrections of the raw data in linear space, for example detector offset and gain corrections and further linear corrections as well known in the CT scanner field. This linear-corrected data 48 is applied to a conversion circuit 50 which transforms linear space to logarithmic $\mu L$ space, where u is the linear absorption coefficient and L is the path length of absorption.

The $\mu L$ space data 52 measured on the subject, hereinafter referred to as measured attenuation data or measured $\mu L$ data, is next applied to a calibration circuit 54 which calibrates the detector channels, including the detectors 32, the A/D converters and the DAS 42. The measured $\mu L$ data is applied to look-up table in the calibration circuit 54 which cross references measured $\mu L$ data to ideal $\mu L$ data where ideal $\mu L$ data takes predetermined system calibration values for each detector into consideration. The ideal $\mu L$ data is applied to a back-projector 56, as well known in the art of CT scanner technology, to generate a final CT image of the subject 26. The back projector 54 includes a convolution filter for convolving the data as required for back projection. The final image of the subject can be suitably stored and/or displayed at the station 58, which in turn preferably includes a display device, such as a digital imaging monitor 60 for providing a digital image on a pixel array, as is well known.

The mathematics of CT reconstruction requires as input the line integrals of desired linear absorption coefficients $\mu$ along measured paths of length L. This quantity is the logarithm of the ideal attenuation along the line in question. When an actual attention is measured, it is the ratio of the transmitted x-ray intensity with the object under study $I_0$ to the transmitted x-ray intensity with the object removed I, as described above. Many real physical effects make the actual attenuation quite different from the ideal attenuation. These effects include beam hardening artifacts, scatter and off-focal artifacts, and partial volumning effects described below.

Simulations reveal that as little as 100 parts-per-million (PPM) of error between adjacent interleaved rays within a convolution will cause noticeable rings near isocenter. For detectors further away from isocenter, the magnitude of these isocentral rings and bands are reduced proportionally to one over the square root of the distance to isocenter as measured in resolution elements which are approximately equal to the detector spacing. Thus, adjacent ray errors between detectors located 4 detectors away from isocenter reduces requirement by ½, and 100 detectors array reduces it by 10, to 1000 PPM. View-to-view errors are even less important with 5000 PPM being quite acceptable.

A ring artifact in a reconstructed CT image is generally caused by a certain detector channel being out of calibration with respect to neighboring detector channels. The calibration method and apparatus of the present invention provides a calibration table for each detector channel to reduce or eliminate the effects of ring artifacts and other artifacts caused by miscalibrated detector channels. This calibration table is applied to the measured data before or during back-projection of the measured data. Projection of measured detector data to form the image is referred to herein as back projection.

Projection from a cross-sectional image to detector data is referred to herein as a forward projection. The present invention employs forward projection of a corrected phantom image to create a reference calibration table for use during interrogation of a subject.

Figure 2:
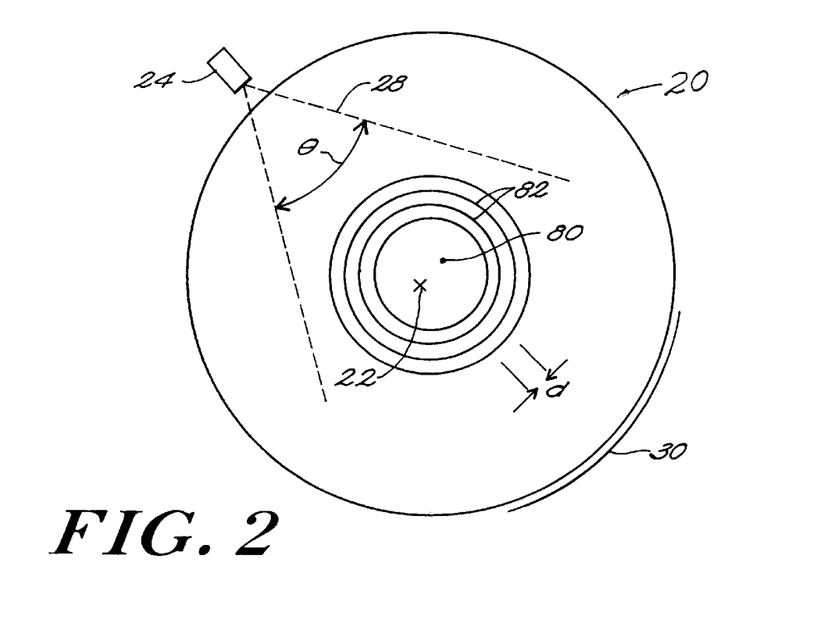
FIG. 2 is an axial view of a CT scanner system collecting calibration data on a phantom in accordance with the present invention.

FIG. 2 illustrates the first step in generating the calibration table in accordance with the method and apparatus of the present invention. A phantom, for example a water phantom 82, is disposed in the scanner 20 in the vicinity of the axis of rotation 22 of the scanner 20. The phantom 82 is preferably, but not necessarily, generally circular in shape and disposed in the scanner 20 such that the center 80 of the phantom is a distance d, for example 3 cm, from the axis of rotation 22. The phantom is preferably comprises water encased in a disk-shaped plastic shell. The spectral absorption characteristics, namely the variation of $\mu$ with x-ray photon energy, of water most closely approximates that of biological tissue, so a calibration based on water is sufficient for examination of human subjects. Note that four water phantoms of different diameters are represented in the illustration of FIG. 2. Only one phantom at a time is imaged for collecting calibration data. Plastic phantom material is preferred because it comprises mostly hydrocarbon and oxygen. Thus, plastic is much like human tissue and water in its spectral absorption characteristics, even though the density is different. The present invention uses the water to calibrate the density via the idealized image, as described below, so even if the exact density of the plastic is unknown, it is measured and therefore compensated for in the present invention.

After the phantom is positioned, the scanner 20 interrogates the phantom, making projections through the phantom at a plurality of discrete orientations. In a preferred embodiment, the scanner makes a projection every ⅛ degree, giving a total of 360*8=2880 projections of the phantom in one revolution, each projection being detected by the detector array 30.

Each detector in the array 30 detects a particular segment of the beam fan 28 during each projection. In a preferred embodiment, there are 384 detectors in the linear array, spaced apart ⅛ degree along the arc. Therefore, the fan angle $\theta$ captured by the detector array is 384*⅛=48 degrees.

Note that in the preferred embodiment described above, the angular increment of the scanner projections and the spacing of each detector element are exactly the same, namely ⅛ degree, so that parallel ray paths from the focal spot to the various detectors from various views result as the scanner rotates about the subject. Because these angles are equal, the measured attenuation data collected can be resorted from 2880 fan beam views to 1440 parallel views of half ray spacing. The consequences of ¼ ray offset allows for back projection of parallel data with rays from detectors on opposite sides of the fan exactly interleaved with each other, doubling spatial resolution. However, these interleaved rays are acquired from views roughly half a scanner revolution apart, and from detectors disposed on opposite side of the fan. In a preferred embodiment, such non-adjacent detectors which produce the neighboring or interleaved rays, and therefore are sometimes referred to as "neighboring" detectors, are precisely calibrated with respect to each other, because they mutually sample nearly the same range of $\mu L$ values, with rays propagating in opposite directions. The rays are the closest in proximity in the parallel-view convolution back-projection process and therefore should be precisely balanced with each other.

It should be appreciated that other projection angles and detector angle spacings can differ from those described without departing from the invention. Further, parallel rays can be provided for the fan beam data using well known parallel rebinning techniques.

An initial step in forming the calibration table in accordance with the present invention is to collect measured $\mu L$ data on a plurality of phantoms. In a preferred embodiment, data is collected on four phantoms 82 of diameter 30 cm, 25 cm, 20 cm, and 16 cm. These phantoms correspond to $\mu L$ values in the range of 6, 5, 4, and 3 respectively, and therefore provide a range of calibration data closely approximating data likely to be collected during interrogation of a human subject. In the preferred embodiment, the centers of each of these phantoms are offset a distance d of 3.2 cm±0.6 cm from the scanner axis of rotation 22.

Note that for purposes of the present invention, the attenuation logarithm data, namely $\mu L$ data, is referred to herein and in the claims as "attenuation data". It is well recognized that $\mu L$ does not directly represent attenuation data, but instead is the logarithm of the attenuation data.

In addition to scanning the four phantoms, a scan of the "empty hole" or "empty scan aperture" is also performed to provide for window compensation data. An X-ray window (not shown) is included in the system to protect the subject from mechanical interference with the rotating source and detector assembly. Typically, the x-ray window is formed as a part of the cover or skin between the scanner and the subject. However, the window carries with it its own imperfections which must be compensated for. For this reason, an empty scanner is imaged, and data as attenuated by the window is collected. This scan is referred to herein and in the art as scanning the "empty hole". Preferably, in accordance with one aspect of the present invention, any data collected during this step is subtracted from the calibration data sets collected on each of the phantoms.

Figure 3:
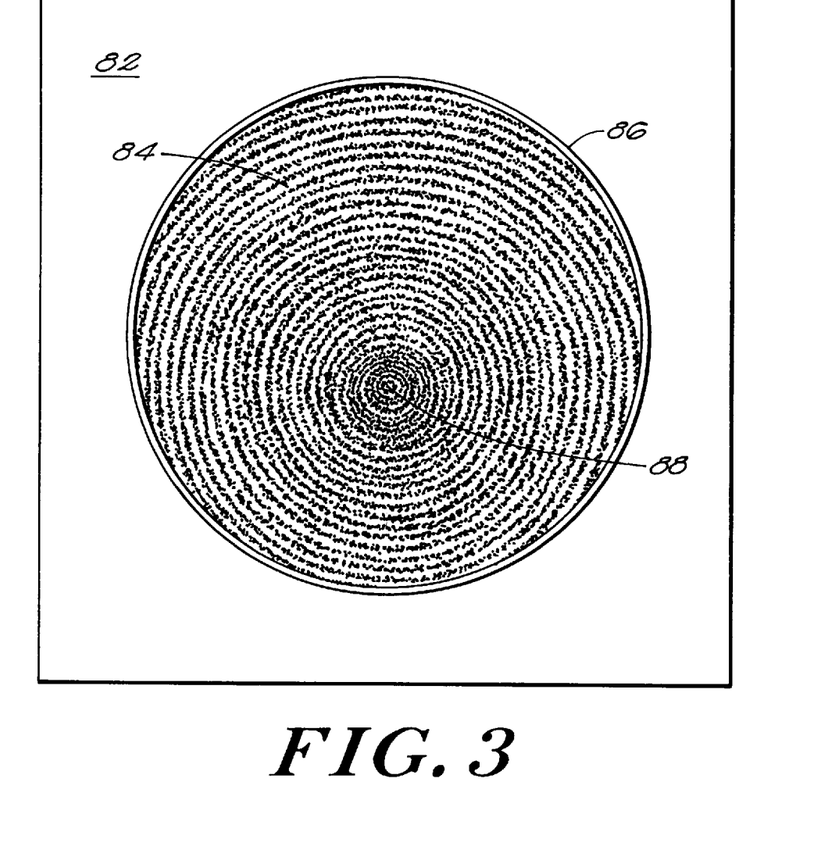
FIG. 3 is a back-projected image of data collected during phantom interrogation in accordance with the present invention.

Measured $\mu L$ data collected on the phantoms is back-projected in accordance with well-known imaging projection techniques to produce a measured image of the phantom, as shown in FIG. 3. Rings 84 are usually visible in this image, due to slightly miscalibrated detector channels and other anomalies in the system. The focal point 88 of the rings 84 is at the center of the source detector frame, called the iso-center, where the ring artifacts are concentrated. In this reading, the phantom center was placed a distance d of 3.2 cm from isocenter. The back projection is performed using a seed of known approximate detector characteristics to smooth out the data, thereby avoiding dishing in the final image.

For forming the ideal image, each of the four measured phantom CT images obtained is first scaled to the average water value to be 0 Hounsfiel units (HU), and the quantum noise is removed from the known water area by forcing all pixel values in the water area to be exactly 0. For example, any pixel values in the range of −20 HU to +20 HU are set to 0 HU. Likewise, pixels corresponding to air are fixed at −1000 HU. Note that in this process the plastic walls are scaled to a proper HU value but they are left with all imperfections, including quantum noise. In this way, any wall imperfections are properly included in the forward-projection process.

Figure 4:
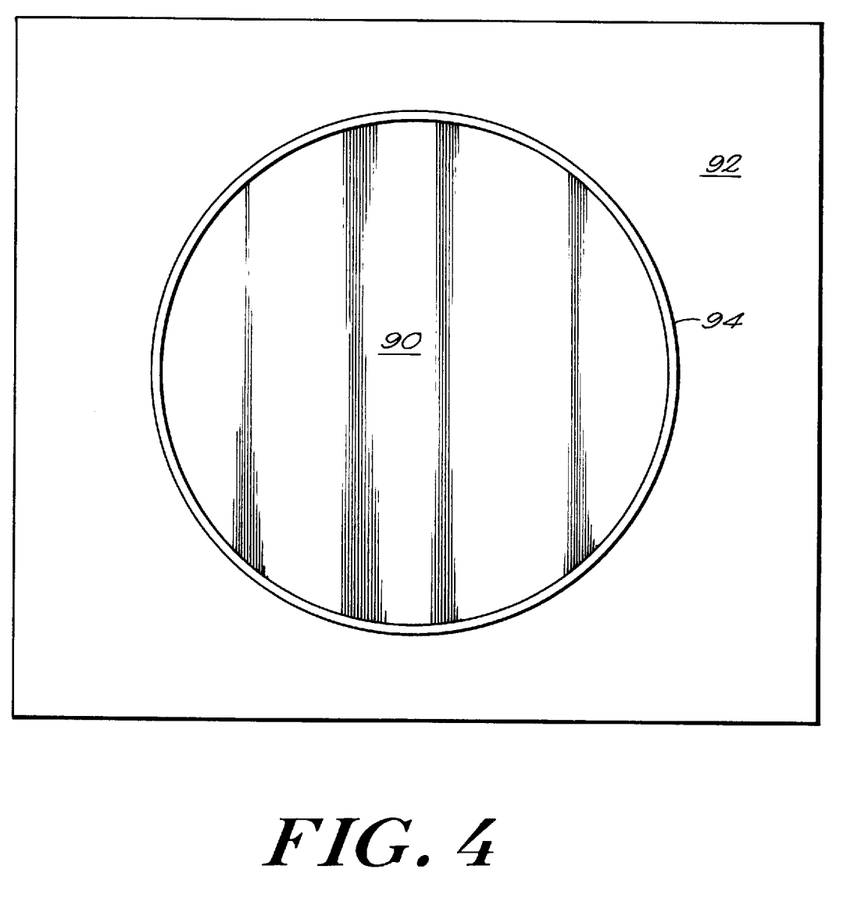
FIG. 4 is a converted ideal image of the data collected in FIG. 3 in accordance with the present invention.

An idealized phantom image is illustrated in FIG. 4. The pixels 90 in the center portion correspond to water and therefore are fixed at a uniform 0 HU. The pixels 92 in the outer portion correspond to air and therefore are fixed at −1000 HU. The pixels 94 corresponding to the plastic rim of the phantom include information related to the geometry of the rim and therefore, the pixel values corresponding to the rim are not adjusted.

The scanner hardware is accurate to within a thousandth of an inch, so the scanner image is used to identify the geometry of the phantom. Even in situations where the phantom includes pockets of air, which would be unacceptable in prior art calibration methods, the present invention is still able to calibrate the system, because any measurements in the region of water, ie −20 HU through +20 HU are set to 0 HU. All that is required for a phantom is a cheap plastic shell filled with water, roughly placed in the path of the beam.

The next step for generating the calibration chart or curve involves a forward projection of the idealized image of FIG. 4. The forward projection is made along exactly the same paths measured to produce the original measured image. This creates ideal $\mu L$ values exactly aligned with the measured $\mu L$ values. This associated data pair of ideal and measured $\mu L$ is exactly the input needed for the remainder of the calibration process of the present invention. The forward projection creates idealized detector $\mu L$ data for each of the detectors across all sensor orientations. For example, in the preferred embodiment of the present invention, a matrix of ideal $\mu L$ data of size 384 by 2880 is created. Therefore, for each of the 384 detectors, ideal data is calculated which after a complete scan of 2880 projections would result in the idealized image. Since there are 2,880 views of data from each of the four phantoms, as many as 11,520 such ordered-pairs per detector are provided. It is these ordered-pairs, segregated by detector which form the input for further processing.

Figure 5:
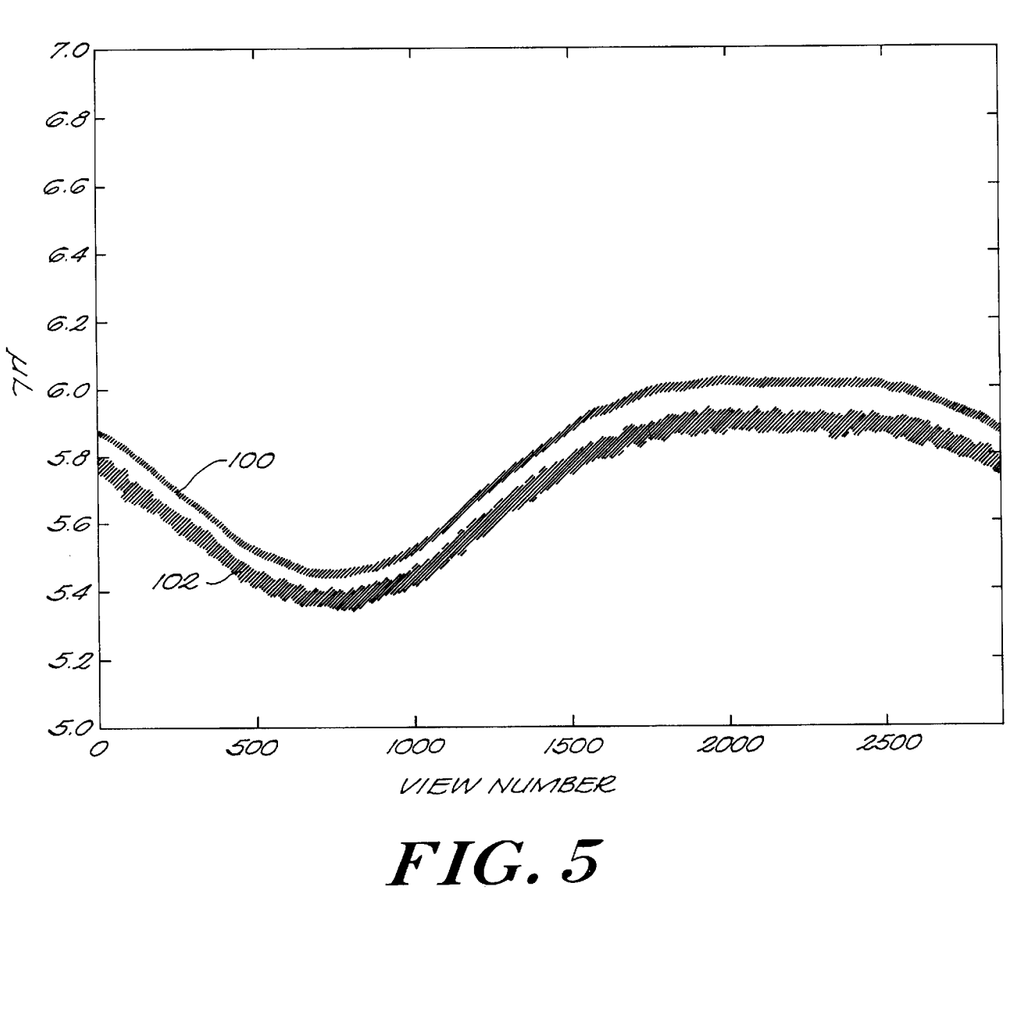
FIG. 5 is a chart or curve of measured attenuation data and forward-projected ideal attenuation data or $\mu L$ values for one of the detectors in the detector array as a function of view number for a single phantom in accordance with the present invention.

The forward-projected ideal data is represented, by way of example, in FIG. 5. FIG. 5 is an example of a typical chart of forward-projected ideal $\mu L$ data 100 and measured $\mu L$ data 102 as a function of view number for a given detector. It can be seen that the ideal data 100 is generally noiseless and that the measured data 102 is generally noisy. In the preferred embodiment, the forward projection of the ideal phantom would result in approximately 320 of such curves, one for each detector whose rays cut deeply enough into at least the largest phantom (⅓ the maximum $\mu L$ for the phantom) to allow calibration of at least one point in the table for that detector. Each view number on x-axis of the chart has an associated data pair of ideal and measured $\mu L$ values.

Figure 6A:
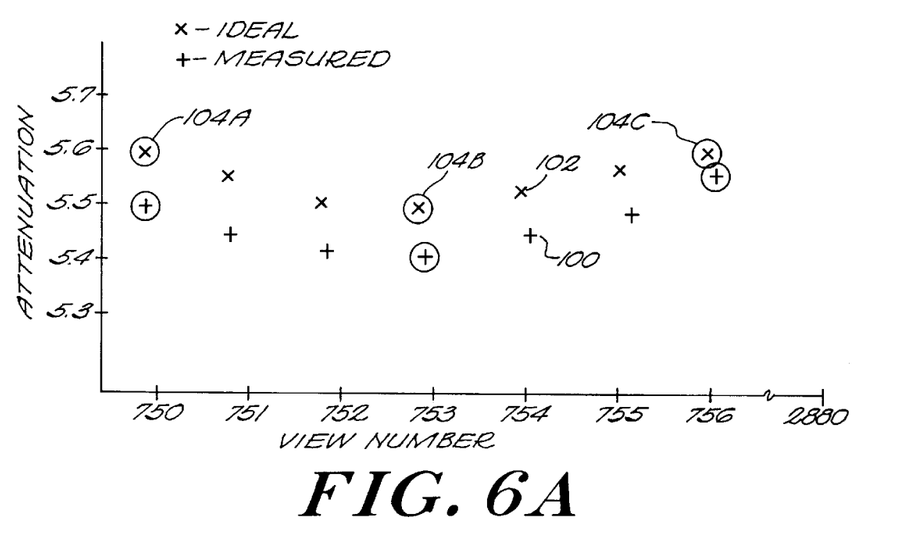
FIG. 6A is a detailed chart of the data of FIG. 5 for views 750 though 756.
Figure 6B:
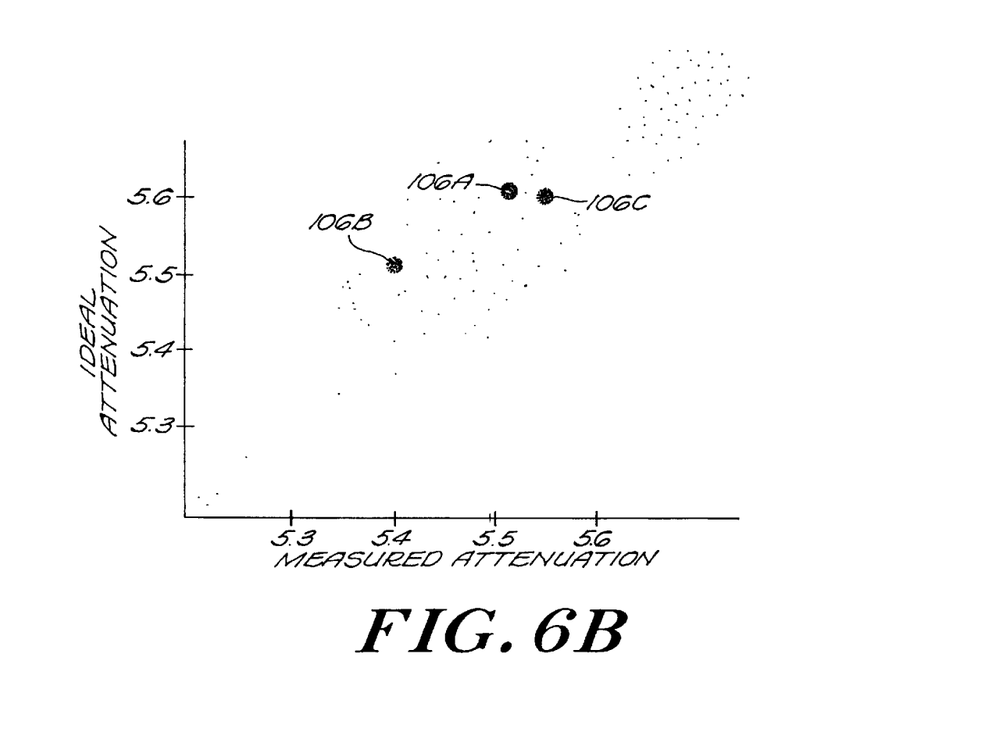
FIG. 6B is a plot of corresponding data pairs from FIG. 6A mapped to a chart of measured values on the X-axis vs. ideal $\mu L$ values on the Y-axis in accordance with the present invention.

FIG. 6A provides a close-up view of the data of FIG. 5, for example between view numbers 750 and 756. Each data pair represents, for a given view, actual measured $\mu L$ data and ideal, forward-projected $\mu L$ data. This data is mapped onto the chart of FIG. 6B as shown. FIG. 6B graphs each data pair, the measured $\mu L$ values 100 being the X-axis and the corresponding forward-projected ideal $\mu L$ values being the Y-axis. Data pair 104A corresponding to view 750 in FIG. 6A is mapped to point 106A on FIG. 6B. Data pairs 104B and 104C likewise map to points 106B and 106C respectively. Each detector has its own associated measured $\mu L$ value versus ideal $\mu L$ value chart. In the preferred embodiment, 384 of these charts are created, one for each detector.

Figure 7:
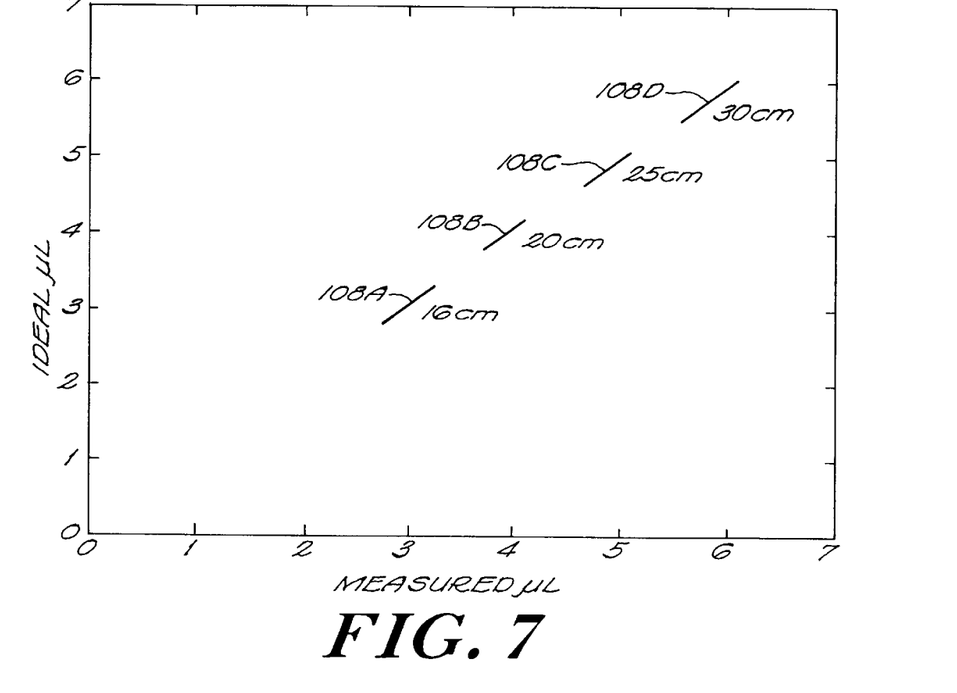
FIG. 7 is a chart of the relationship between the ideal $\mu L$ values and measured $\mu L$ values for a single detector in the detector array for calibration data collected on four phantoms in accordance with the present invention.

FIG. 7 is an expanded view of the data of FIG. 6, spanning a larger range of $\mu L$ values. The four portions of the curve represent collections of $\mu L$ data corresponding to the four phantoms scanned to collect the data. In the preferred embodiment, each collection 108A –108D includes 2880 data pairs, and there are a total of 384 collections, one for each detector. Typical human patient $\mu L$ values range between 0 and 3.5 for a head scan and between 0 and 7 for a body scan. Generally, larger subjects result in larger $\mu L$ values.

FIG. 7 illustrates a typical set of compressed data pairs for a detector element near the central channel, for example, element 153 out of 384. This chart represents a non-linearity calibration for each detector. In the preferred embodiment, 384 of such curves would result, one for each detector. In FIG. 7, dense regions 108A–108D having many calibration points are separated by sparse regions with no calibration points. This graph illustrates a fundamental practical problem with calibration of third generation machines. Namely, with so many gaps between calibration points, the challenge is to determine the proper calibration values between points. Prior art methods are forced to assume a functional form, typically some power polynomial. Instead, the present invention solves this problem without such limitations. To understand how this is possible, it is important to realize that the data for channel 153 corresponds with the data of its neighbor, channel 152 for example, to better than a 90% overlap in measured values. This ensures that whatever value is chosen for a calibration of one of these neighbors, the other neighbor will get a matched value. If exactly centered cylindrical phantoms had been scanned, there would have been no overlap, and 100 PPM agreement would have been difficult if not impossible.

But this 90% overlap between calibration points for neighboring detectors can be improved. For improved precision, the detectors can be interleaved from the other side of isocenter, as for example with a quarter detector width shift, and matched accurately. It has been determined that there is also a better than 90% overlap between calibration data for this interleaved detector and its two neighboring ray detectors on the other side of the fan. Although the absolute calibration of detectors is certainly not this accurate, the relative calibration of neighboring rays is, and this is what prevents rings.

In a preferred embodiment, noise compression is performed on the data of FIG. 7. Noise compression involves dividing the ideal $\mu L$ axis into a number of bins, for example 1024 bins in the preferred embodiment. The reason for this is that the forward projection data along the ideal axis is known very accurately, while the measured data along the x-axis is noisy, as seen in FIG. 5. The choice of 1024 is a practical one; it must provide a sufficiently fine selection such that the following noise compression process does not put unacceptable discontinuities in the processed data, and sufficiently coarse selection such that several input points will be found in each significant bin. If there are more than two observed data pairs within a bin they are compressed to an average measured μL value for that ideal μL bin. If there are fewer observed data pairs, they are considered statistically unreliable and are discarded.

Any data pairs with very low μL are also discarded since they correspond to rays very near the edge of the phantom, where the effects of off-focal radiation corrupt the data. In a preferred embodiment, μL values less than one-third of the maximum μL of the phantom are discarded. In addition, data is discarded where uncorrected detector position errors have their greatest effect.

Figure 8:
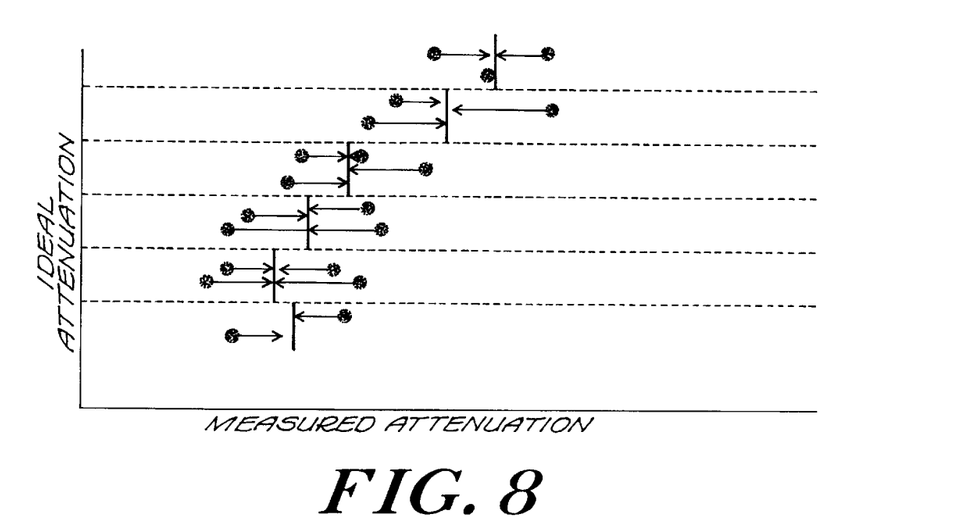
FIG. 8 illustrates the operation of noise compression on the data of FIG. 7 in accordance with the present invention.
Figure 9:
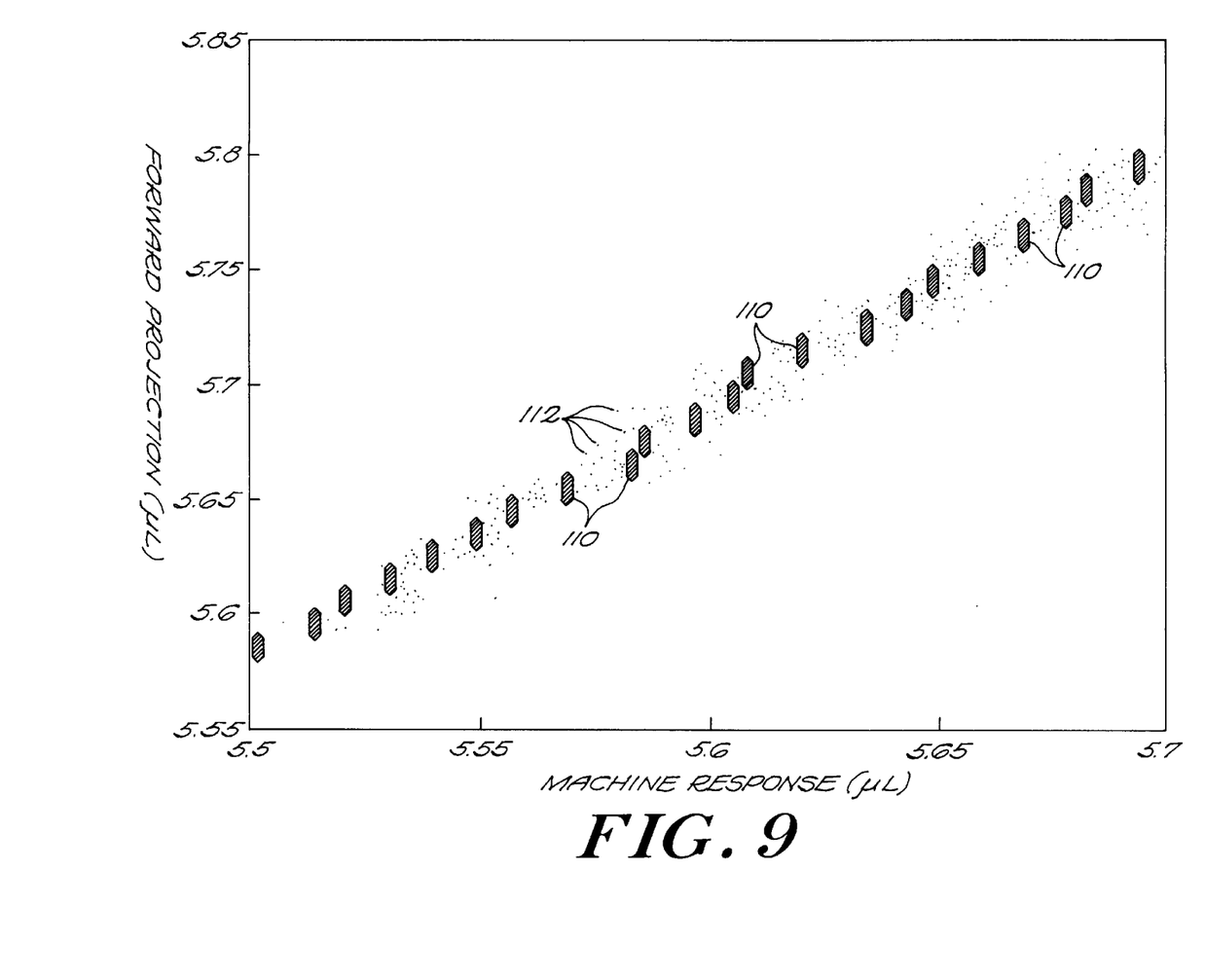
FIG. 9 is an expanded view of noise compressed data in accordance with the present invention.

FIG. 8 is a detailed chart of data points binned along the ideal axis. FIG. 9 is a chart of noise compressed data 110 resulting from compression of the measured μL data 112 in the μL value range of 5.5 to 5.9. In the preferred embodiment, there are still 2880 data pairs in the noise compressed data. The μL value range of the highest of the noise compression bins is set well beyond the point at which data would be expected for the phantom, and the lowest of the bins is arbitrarily chosen between zero and the lowest point at which data would be expected. The collected μL values in each bin is averaged for the bin (so as to provide noise compression) and the average value for each bin is used in the next steps.

The next step in generating the calibration chart involves interpolation between known phantom data and extrapolation beyond the largest known μL values. A seed chart or curve is used for this purpose. The first calibration value is zero by definition. It corresponds to a window scan of an empty hole, and ideal μL is by definition zero for an empty hole.

Instead of using a seed, prior art methods assume that the data can be approximated by some form of polynomial. The reason for this is that the prior art methods have no other choice because data is collected over a few sparse discrete locations of attenuation. The attenuation curve is a function of the X-ray tube, the window, filters, radiation damage on the solid state detector, the wrapper of the detector, energy-dependence of the photodiodes and other anomalies. It is quite a jump to assume that all these factors can be approximated accurately by any polynomial. Prior art techniques interpolate based on this polynomial.

A phenomenologically determined seed curve is employed to interpolate between clumps of calibration data and extrapolate beyond them. The seed curve represents the average results of prior calibrations with similar detector types. The differences or deltas Δ from the averaged seed are determined and the deltas are linearly interpolated between clumps to reach the final non-linearity calibration curve for each detector. Similarly, the deltas are extrapolated to complete the non-linearity calibration curve beyond the highest clump and interpolated from the lowest accepted μL clump to 0 μL where a 0 value is set. This process is repeated for all detectors having sufficient calibration data.

Figure 10:
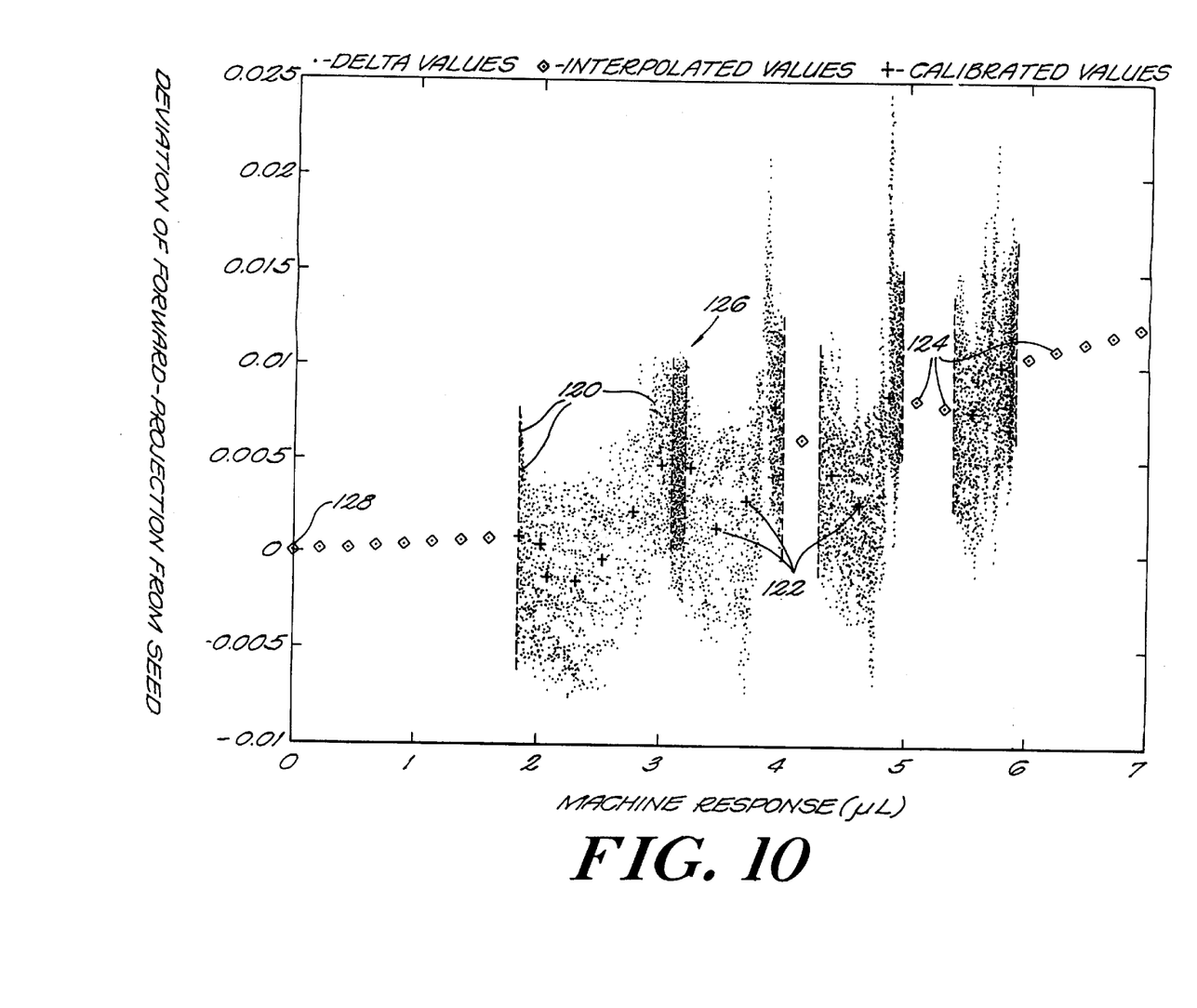
FIG. 10 is a chart of deviation of the forward projected values from the seed as a function of measured gL values in accordance with the present invention.

The graph of FIG. 10 shows 2880 delta values for each of the four phantom diameters of the preferred embodiment—16, 20, 25, 30 cm. The delta values are represented as dots 120 in FIG. 10. The delta values are first calibrated, shown as "+" signs 122 in the chart of FIG. 10 for any measured μL values resulting in calibration data. Next, delta values are interpolated between and extrapolated beyond the captured data points—as shown in the diamond-shaped signs 124 of FIG. 10. Note that the detector used to collect this data is removed far enough from isocenter that the off-centered phantoms overlap, as demonstrated in region 126. Note also the complete freedom from any polynomial form in the collected data. This demonstrates why systems which rely on polynomial fit for calibration data are less accurate. Note also that at 0 μL, the delta value is forced to zero.

Figure 11:
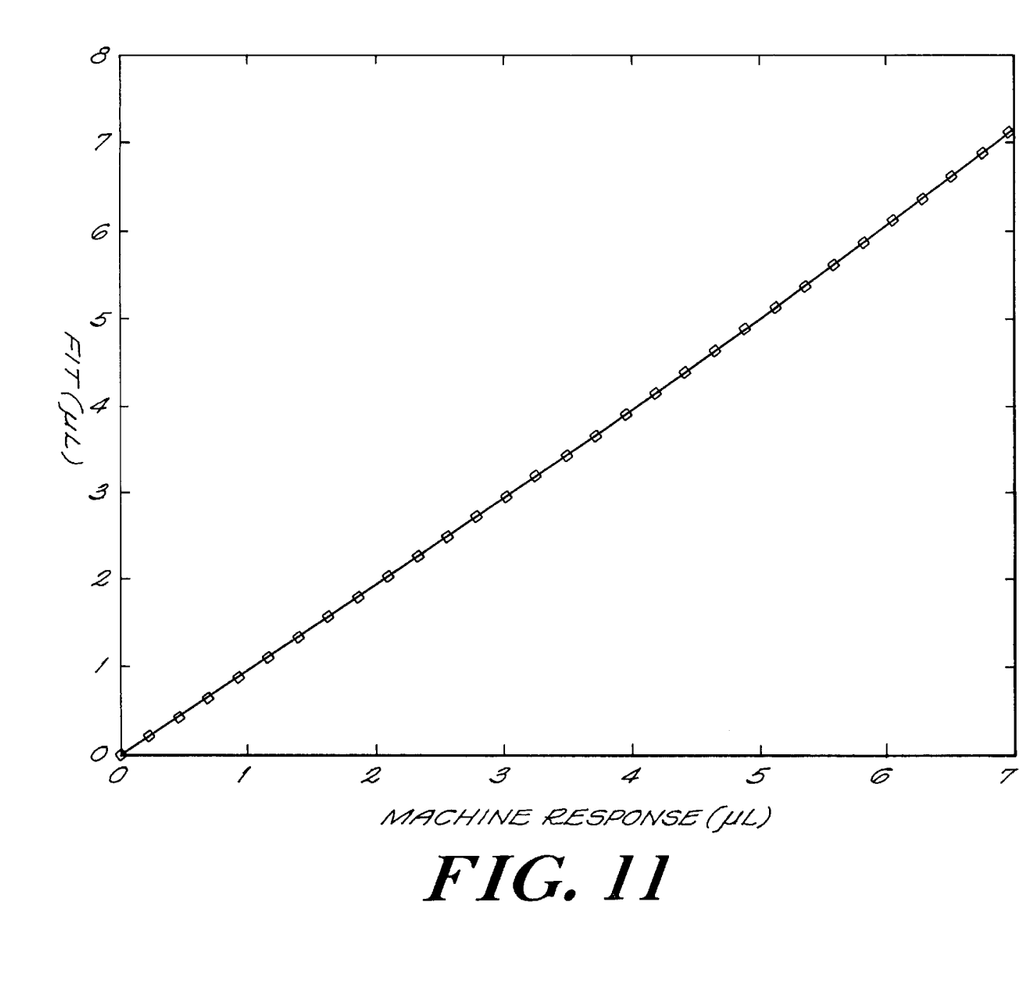
FIG. 11 illustrates the calibrated values versus the seed values for the data of FIG. 10 in accordance with the present invention.
Figure 12:
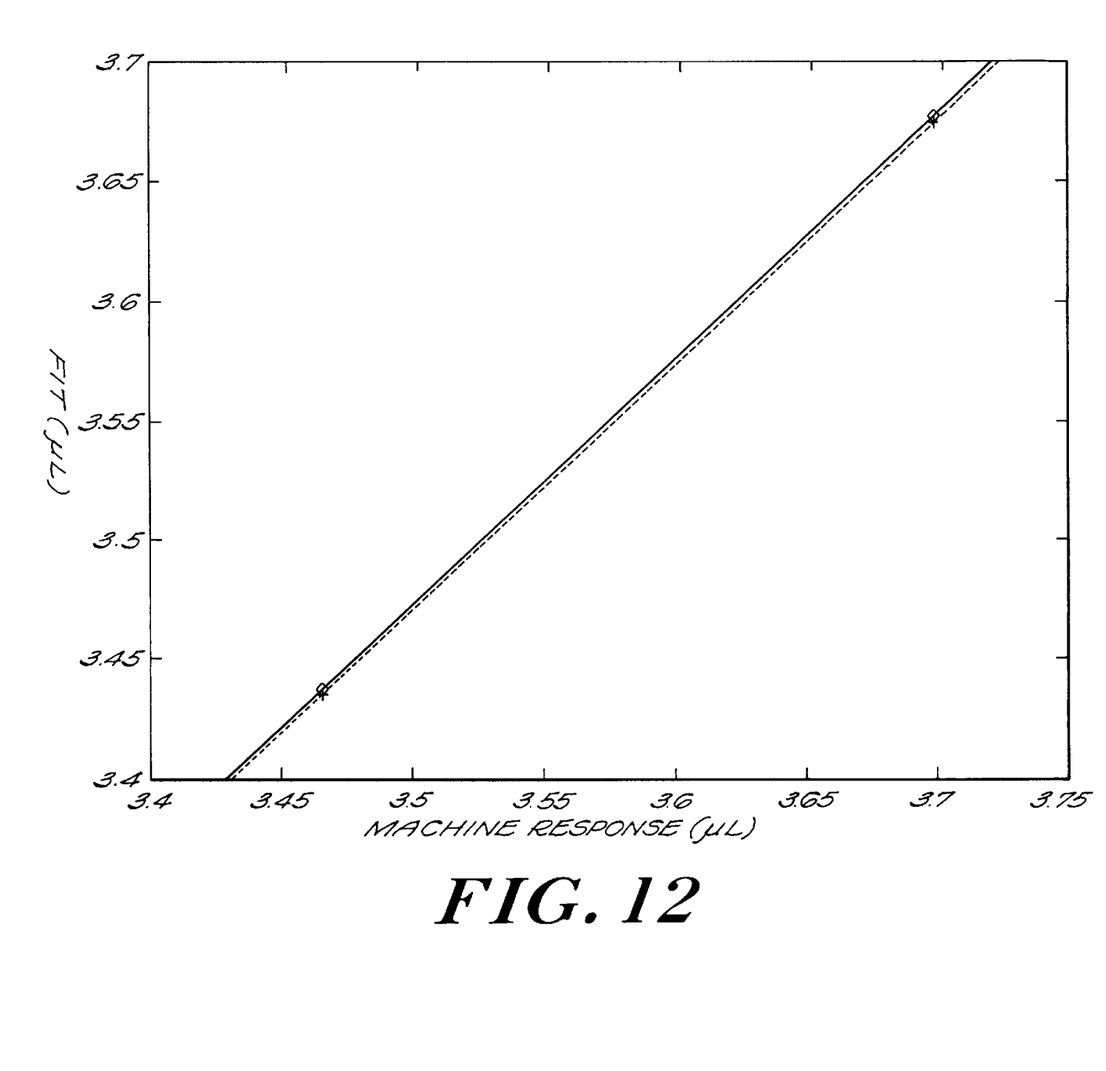
FIG. 12 is a detailed view of the data of FIG. 11 in accordance with the present invention.

FIG. 11 is a graph representing piecewise linear fit of μL resulting from interpolation and extrapolation of the collected data using a seed curve. The chart demonstrated that the two match to a high level of accuracy. 100 PPM difference between the two is not visible in this expanded view. FIG. 12 is a detailed section of FIG. 11 which shows the difference between μL values ranging between 3.4 and 3.7.

Detectors having insufficient calibration data are calibrated from their inner neighbors having sufficient calibration data. In an experimental embodiment, the fourth from last detector individually calibrated was used for calibration of the outer detectors. Since these rays are quite far from isocenter, the ring and band artifacts remaining are within specification, although larger calibration phantoms could be employed. This is a practical tradeoff between calibration complexity and ultimate image quality.

Calibration based on the seed works to a high degree of accuracy because, the seed is based on the characteristics of the detectors used, which are known to a high level of accuracy. The response curve of each detector is also known, along with the detector's response to the phantom interrogation. The seed is essentially used as a draftsman's curve to shape the μL response curve between known, measured data points. Nothing is assumed about the seed except that the detector response is known to a high degree of accuracy. The interpolated values between known data points are based on deviations or deltas from the behavior of the seed in that region.

The interpolated chart is next subject to a triangular weighting to compress the curve to a manageable calibration table—for example 64 points. The remaining compressed measured μL versus ideal μL data pairs for each detector are assembled individually. In a preferred embodiment, each detector-specific set is independently set to a 64-point piecewise linear lookup table. The lookup table is structured for rapid use with the measured μL as the x-axis (independent variable) and the ideal μL as the y-axis (dependent variable). Rapid calculation of the ideal from the measured μL data is possible. The x-axis quantization election of 64 data points is adequate for present imaging quality, but higher values, for example 128 would lead to greater precision.

Figure 13:
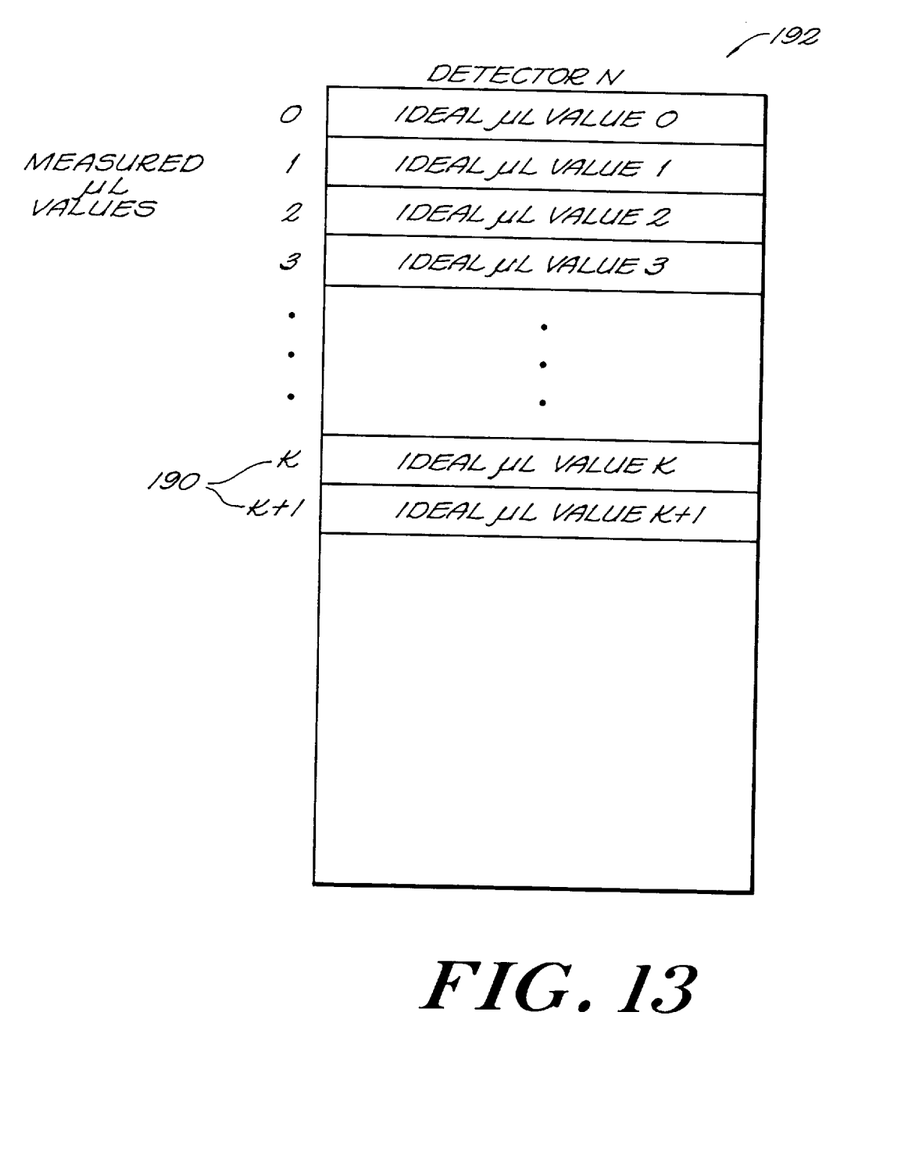
FIG. 13 is an example look-up table for use during imaging of a subject in accordance with the present invention.

The calibration table 192, as illustrated in FIG. 13 is used during scanning of a patient. When μL data is captured on the subject, the measured μL data 190 for each sensor is quantized and referenced into the table 192. When a measured μL data element arrives it is converted to an ideal μL value 194 according to the lookup table 192. A piecewise linear interpolation is performed between nearest ideal values to generate the ideal μL value corresponding to the measured μL value. An ideal μL value for that detector is returned and used in the image.

In prior art systems which center the phantom on the axis of rotation, each detector only captures a single data point along the correction curve for each phantom. In other prior art systems which offset the center of the phantom from the system axis, data points over a wider range of attenuation values can be collected, but the calibration data is conformed to a phenomenological function to connect the points, for example a polynomial curve. A polynomial characterization curve assumes that the machine is perfect. If the detectors or A/D converters, or other hardware are not quite linear in operation, the calibration will be off. In the present invention, each individual detector is calibrated according to a look-up table, independent of all other detectors. This results in compensation for detectors which are not exactly alike. Therefore, quality control of detectors can be alleviated, reducing system costs.

In a preferred embodiment of the present invention, the outermost detectors do not get calibrated, rather, the calibration of the outermost detectors is extrapolated from the inner detectors. The phantom is utilized to ⅓ of its major diameter. Any readings beyond this are removed from consideration. Precision required—gain balance—is 1/(distance from center)½. Precision in the center detectors must be very accurate, to within 100 PPM. The outer detectors are less sensitive. While it would be extremely accurate to calibrate all detectors, for the sake of efficiency it is sufficient to calibrate the outermost detectors by extrapolation from the innermost detectors.

In a third generation CT scanner, the source and each detector are fixed relative to each other and rotate about the object being imaged. This means that the rays between the source and each detector form tangents to circles around the axis of rotation. When the system rotates, the rays track together and form tangents to a circle. With precisely-centered phantoms, as in the prior art calibration methods, all path lengths for each detector will be identical, resulting in a calibration for only that one path length—$\mu L$. The techniques which employ centered phantoms, need a single $\mu L$ measurement, because these techniques generally employ plastic phantoms. The plastic phantoms are generally non-uniform, as described above. Therefore, the prior art techniques average over all $\mu L$ values for each detector remove the effects of imperfections in the phantom.

Because more data points are collected, the present invention makes no assumptions about the behavior of the $\mu L$ curve, so the detectors and A/D channels can be different from one another. The present invention calibrates out these differences, so long as the response of each individual detector is generally constant. Each detector is calibrated independently of all the others, and as a result, the detector calibration curves have only one thing in common, namely they are interpolate and extrapolate via the same seed. With regard to the data there is no incest across detectors, therefore no assumption as to the form of the data, for example a polynomial, is made.

In a preferred embodiment, there is a ⅛ degree separation between detectors in the fan, and a ⅛ degree separation between view samples. Therefore, the data can be sorted into sets of parallel rays. The rays correspond to detectors, but each parallel ray is taken during a different view, so subsequent views, and adjacent detectors result in the same ray angle, and because it is the same angle, parallel ray result. The rays represent the paths along which data was collected.

By introducing a ¼ ray shift into the scanner, the rays propagating through the subject become interleaved. The net result is that data collection becomes a collection of parallel rays. Detectors on opposite sides of the fan interleave. For this reason the present invention not only calibrates adjacent detectors, but also calibrates "neighboring" detectors on opposite sides of isocenter. Prior art techniques are unable to do this.

Because the technique of the present invention images forward projects the idealized image of the phantom, each neighboring parallel interleaved ray contribute to the same true picture. Neighboring rays will measure approximately the same , $\mu L$ values in the phantom, and therefore they will calibrate to a high level of precision.

The greatest precision is required in the center of the image. Ring artifacts tend to be circular rings. If the artifact is an outer ring, the error is spread over a large area, and therefore any given point on that large ring represents a small error. But for a small ring, concentrated in the center, the error will be more apparent in the final image.

In the center of the image, 100 PPM accuracy is needed. But at the center of the image, the $\mu L$ values are bunched, and therefore the high level of precision is achieved where it is needed the most. For this reason, it is important to calibrate neighboring rays, so even if the absolute value of overall system accuracy is at 5000 PPM, ray-to-ray accuracy for interleaved rays is still within 100 PPM.

To achieve the statistical precision of 100 PPM required for ring-free images two rotation scans of maximum power, for example 50 mA are desired. This provides a sufficient number of detected photons to produce nearly ring-free images for all four phantom diameters. If higher power protocols were employed, the scan power should be increased proportionally.

Interpolation is performed in the present invention only in regions of the $\mu L$ curve which do not have data. The interpolation in the present invention is based on a seed curve representative of the behavior of the detectors. The prior art employs a polynomial curve to fit all data, including known data, which may or may not fit exactly on the data.

The present invention creates a fast access look-up table for direct cross-referencing of measured $\mu L$ data to ideal $\mu L$ data. This technique offers distinct speed and accuracy advantages over prior art techniques which focus on determining the coefficients of polynomials which characterize the data in a time consuming and relatively inaccurate procedure.

While this invention has been particularly shown and described with references to preferred embodiments thereof, it will be understood by those skilled in the art that various changes in form and detail may be made therein without departing from the spirit and scope of the invention as defined by the appended claims.

What is claimed is:

1. A method for calibrating radiation detectors in a computed tomography (CT) scanner comprising the steps of:

directing a radiation beam at a plurality of radiation detectors through a phantom having known attenuation characteristics, the phantom attenuating the beam and the detectors generating measured attenuation data therefrom;

back-projecting the measured attenuation data to generate a measured phantom image;

converting the measured phantom image to an ideal phantom image using the known phantom characteristics;

forward-projecting the ideal phantom image to generate ideal attenuation data; and generating calibration values for each detector by cross-referencing corresponding ideal attenuation data and measured attenuation data.

2. The method of claim 1 wherein the step of directing a radiation beam comprises directing an X-ray beam.

3. The method of claim 1 further comprising the step of disposing a phantom of imprecise geometry in the beam path.

4. The method of claim 1 further comprising the step of positioning the phantom at a position other than a center position of the scanner.

5. The method of claim 1 further comprising the step of disposing a water phantom in the path of the beam, the water phantom comprising a plastic shell of unknown attenuation characteristics containing water of known uniform attenuation characteristics.

6. The method of claim 1 wherein the step of calibrating further comprises the step of interpolating between cross-referenced ideal and measured attenuation data using a seed chart of known detector characteristics as a guide.

7. The method of claim 6 wherein the step of interpolating is applied to the ideal and measured attenuation data only where no data has been collected.

8. The method of claim 1 further comprising following the step of forward projecting, compressing the cross-referenced corresponding measured and ideal attenuation data to reduce the effects of noise in the calibration data.

9. The method of claim 1 wherein the step of back-projecting the measured attenuation data includes the step of approximating beam hardening characteristics of each detector.

10. The method of claim 1 further comprising the steps of:
scanning a subject with the scanner, the subject attenuating the beam to generate measured subject data;
applying the measured subject data to the calibration values to generate calibrated measured subject data;
back-projecting the calibrated measured subject data to generate a calibrated subject image.

11. The method of claim 1 further comprising the step of generating calibration values by scanning a plurality of phantoms of various sizes.

12. A system for calibrating radiation detectors in a computed tomography (CT) scanner comprising:
a radiation source for generating a radiation beam;
a phantom of known attenuation characteristics for attenuating the beam;
a plurality of radiation detectors for detecting the radiation beam and generating measured attenuation data therefrom;
a back projector for projecting the measured attenuation data to generate a measured phantom image;
a converter for converting the measured phantom image to an ideal phantom image using the known phantom characteristics;
a forward projector for projecting the ideal phantom image to generate ideal attenuation data; and
a circuit for generating calibration values for each detector by cross-referencing corresponding ideal attenuation data and measured attenuation data.

13. The system of claim 12 wherein the radiation beam comprises an X-ray beam.

14. The system of claim 12 wherein the phantom is of imprecise geometry.

15. The system of claim 12 wherein the phantom is positioned at a location other than the scanner rotation axis.

16. The system of claim 12 wherein the phantom comprises a water phantom comprising a plastic shell of unknown attenuation characteristics containing water of known uniform attenuation characteristics.

17. The system of claim 12 further comprising a seed chart of known detector characteristics for interpolating between cross-referenced ideal and measured attenuation data.

18. The system of claim 12 further comprising a noise compression circuit for reducing the effects of noise in the calibration data.

* * * * *